United States Patent
Stephan

(10) Patent No.: US 10,197,536 B2
(45) Date of Patent: Feb. 5, 2019

(54) METHOD FOR DETECTING DAMAGE TO A HOLLOW SHAFT

(71) Applicant: BASF SE, Ludwigshafen (DE)

(72) Inventor: Oskar Stephan, Hockenheim (DE)

(73) Assignee: BASF SE, Ludwigshafen (DE)

( * ) Notice: Subject to any disclaimer, the term of this patent is extended or adjusted under 35 U.S.C. 154(b) by 743 days.

(21) Appl. No.: 13/891,559

(22) Filed: May 10, 2013

(65) Prior Publication Data

US 2013/0298684 A1 Nov. 14, 2013

Related U.S. Application Data

(60) Provisional application No. 61/645,643, filed on May 11, 2012.

(51) Int. Cl.
*G01N 29/11* (2006.01)
*G01N 29/44* (2006.01)

(52) U.S. Cl.
CPC ......... *G01N 29/11* (2013.01); *G01N 29/4427* (2013.01); *G01N 2291/101* (2013.01); *G01N 2291/2634* (2013.01)

(58) Field of Classification Search
CPC ............... G01N 29/11; G01N 29/4427; G01N 2291/2636; G01N 2291/044; G01N 29/07; G01N 29/2487; G01N 29/043
USPC ........................ 73/627, 629, 596–598, 602
See application file for complete search history.

(56) References Cited

U.S. PATENT DOCUMENTS

| 3,955,405 A | * | 5/1976 | Couture | G01N 29/0627 340/659 |
| 4,593,568 A | * | 6/1986 | Telford | F22B 37/003 376/252 |
| 4,893,511 A | * | 1/1990 | Voigt | G01N 29/265 73/622 |
| 5,992,236 A | * | 11/1999 | White | G01N 29/043 73/622 |
| 6,145,376 A | * | 11/2000 | Elgee | B65H 7/02 73/159 |
| 6,360,599 B1 | * | 3/2002 | Pathak | G01C 13/008 181/124 |
| 7,378,452 B2 | | 5/2008 | Long et al. | |

(Continued)

FOREIGN PATENT DOCUMENTS

| DE | 3728369 A1 | 3/1989 |
| DE | 19952407 A1 | 5/2001 |

(Continued)

OTHER PUBLICATIONS

English Translation of EP2546642, Description EP2546642.*
International Search Report in international application No. PCT/EP2013/059114, dated Jun. 13, 2013 (English translation).

*Primary Examiner* — Son T Le
*Assistant Examiner* — Tarun Sinha
(74) *Attorney, Agent, or Firm* — Marshall, Gerstein & Borun LLP

(57) ABSTRACT

A method for detecting damage to a hollow shaft is disclosed. A sensor for transmitting and receiving a signal is positioned at an end face of the hollow shaft, a signal is transmitted and an echo of the signal is received, the signal propagation time from the time of transmitting the signal until receiving the echo is determined, and the signal propagation time is compared to a predetermined intended value, and with a warning being emitted in the case of a deviation.

11 Claims, 1 Drawing Sheet

(56) References Cited

U.S. PATENT DOCUMENTS

| | | |
|---|---|---|
| 7,851,550 B2 | 12/2010 | Kadonaga et al. |
| 8,070,351 B2 | 12/2011 | Stueven et al. |
| 2003/0061880 A1* | 4/2003 | Bazarov ............... G01M 3/005 73/592 |
| 2009/0320599 A1 | 12/2009 | Burat et al. |
| 2010/0031751 A1* | 2/2010 | Perkins ............... G01N 29/11 73/622 |
| 2010/0180683 A1 | 7/2010 | Lesage et al. |
| 2010/0212428 A1* | 8/2010 | Maeda ............... G06F 3/0202 73/597 |
| 2011/0087444 A1* | 4/2011 | Volker ............... G01N 29/043 702/39 |
| 2012/0191377 A1* | 7/2012 | Engl ............... G01N 29/069 702/39 |
| 2013/0066019 A1 | 3/2013 | Okuda et al. |

FOREIGN PATENT DOCUMENTS

| | | |
|---|---|---|
| EP | 0 304 394 A2 | 2/1989 |
| EP | 1 811 282 A1 | 7/2007 |
| EP | 2 546 642 A2 | 1/2013 |
| JP | S49028077 A | 3/1974 |
| JP | 2010530529 A | 9/2010 |
| JP | 2011516887 A | 5/2011 |
| WO | WO-2009/129016 A2 | 10/2009 |
| WO | WO-2011/115216 A1 | 9/2011 |

\* cited by examiner

METHOD FOR DETECTING DAMAGE TO A HOLLOW SHAFT

CROSS REFERENCE TO RELATED APPLICATIONS

This application claims the benefit of U.S. Provisional Patent Application No. 61/645,643, filed May 11, 2012, incorporated herein by reference in its entirety.

DESCRIPTION

The invention relates to a method for detecting damage to a hollow shaft, wherein the hollow shaft has no radially encircling notches, openings or channels.

Shafts are used in all apparatuses that have rotating components. In this case, the shafts are driven. Within the scope of saving material, it is conventional to use hollow shafts in large apparatuses in particular. Hollow shafts are also used if, for example, it is necessary to cool or heat the shaft.

When used in kneaders or dryers in particular, the shafts comprise functional elements, e.g. hooks or paddles, on their external circumference, by means of which functional elements the material to be dried or kneaded is moved. As a result of this, a force is exerted on the shaft via the functional elements and it can result in damage to the shaft. In this case, it firstly is material fatigue phenomena which are important, as are e.g. material defects as well, which can initially lead to cracks. As a worst case scenario, such cracks can lead to the shaft breaking and hence lead to irreparable damage to the plant in which the shaft is used.

In order to avoid such damage to the shaft, it is necessary to inspect the shaft regularly in respect of damage, in particular in respect of cracks which are not visible from the outside. To this end, use is usually made of ultrasound measurement methods. To this end, the entire surface of the shaft casing is scanned in conventional methods, with defects leading to a modified reflection of the echo and hence to a signal indicating such damage. However, a disadvantage of this method is that it is necessary to remove the shaft from the plant for inspection purposes or to open up the corresponding apparatus in order to obtain access to the shaft. A further disadvantage lies in the great time expenditure that is required as a result of the inspection over the whole casing length. In addition to the measurement on the outer surface, it is also known in the case of a hollow shaft to carry out the measurement from the inner side. By way of example, this is described in DE 199 52 407 A1. However, it is also disadvantageous in this case that, particularly in the case of long shafts, many measurements have to be carried out before the whole shaft has been measured.

In order to inspect cracks in a turbine shaft, DE-A 37 28 369 has disclosed the practice of coupling a probe with an attachment wedge to the end face of the shaft. The probe emits ultrasound pulses with specific frequencies and is moved in front of the end face by means of a mechanical device. Here, the utilized shafts are usually solid shafts, and the attachment wedge sets an angle at which signals are transmitted from the end face in the direction of the surface of the shaft. Here, the angle is set such that the whole shaft can be detected from the end face. However, the described method cannot be used for a hollow shaft, which only has a thin wall strength. It is particularly problematic that a small angle of the probe already leads to the signal not passing through the whole length of the shaft and hence the shaft cannot be inspected for damage over the entire length thereof.

It is therefore an object of the invention to provide a method for detecting damage to a hollow shaft which can be performed reliably and without removing the shaft.

The object is achieved by a method for detecting damage to a hollow shaft, wherein the hollow shaft has no radially encircling notches, openings or channels, said method comprising the following steps:

(a) positioning a sensor for transmitting and receiving a signal at an end face of the hollow shaft,
(b) transmitting a signal and receiving an echo of the signal,
(c) determining the signal propagation time from the time of transmitting the signal until receiving the echo,
(d) comparing the signal propagation time to a predetermined intended value and emitting a warning in the case of a deviation.

As a result of the method according to the invention it is possible to inspect a shaft even in the assembled state. Unlike the methods known from the prior art, it is unnecessary to remove the shaft for the inspection. Nor is it necessary, for example in the case of a large apparatus which comprises the shaft, to completely expose the shaft in order to carry out a measurement. It is already sufficient to expose an access to an end face of the shaft. The access to the end face of the shaft then enables the measurement to be carried out. By way of example, to this end it is possible to hold the utilized sensor at one position and to rotate the shaft once in order to make a measurement about the whole circumference thereof.

In order to use the method according to the invention particularly for shafts whose wall strength is small compared to their length, it is furthermore advantageous if the end face of the shaft has an angle with respect to the axis of the shaft, which angle lies in the range between 89 and 91°, more preferably in the range between 89.95 and 90.05°. As a result of the corresponding angle between the end face of the shaft and the axis of the shaft it is possible to ensure that the signal penetrates the shaft casing over the whole shaft length and reaches the end of the shaft. This affords the possibility of detecting damage in the shaft, for example cracks in the shaft, at any point.

In order to detect cracks at any position in the casing, it is furthermore advantageous if the sensor is positioned in a region between the radial distance of the inner face of the casing with respect to the axis and the radial distance to the outer face of the casing with respect to the axis on the end face of the shaft. In this case, it is furthermore possible, for example in the case of a relatively thick wall strength of the casing, to displace the sensor in the region between the inner face of the casing to the outer face of the casing. At the same time, as already mentioned previously, the sensor should be moved over the circumference of the casing. This can be brought about either by moving the sensor over the circumference of the casing or, alternatively, by holding the sensor at one position and the shaft carrying out a rotation. In this case, it is particularly advantageous if the shaft is respectively moved on a little in a stepwise manner and another measurement is then carried out so that the sensor remains at one position during a measurement.

A sensor operating according to the pulse/echo method is preferably used as sensor. Such sensors emit a signal and receive an echo of the signal which is reflected at a discontinuity, e.g. at a crack or a shrink hole. The signal emitted by the sensor is preferably a sound signal. More particularly, the signal is an ultrasound signal and the sensor is an ultrasound sensor.

A suitable ultrasound sensor that can be used to carry out the method for example has an operating frequency in the range between 0.1 and 1 MHz. By way of example, a suitable sensor is a sensor which operates with a frequency of 0.5 MHz in a composite variant. By way of example, a probe B1F from GE Measurement & Control Solutions can be used for this purpose.

The method according to the invention is particularly suitable for hollow shafts having a length in the range between 2 and 16 m, more particularly in the range between 3 and 12 m. By way of example, such hollow shafts find use in paddle dryers, disk dryers or kneaders. Such hollow shafts can also be used in other apparatuses, as are used e.g. in chemical apparatus construction and plant constructions. Depending on the use of the shaft, it is possible that functional elements, e.g. paddles, disks or kneading elements, are welded onto the shaft. By suitably positioning the sensor it is also possible in the process to identify e.g. damage to welding seams by means of which the functional elements, e.g. paddles, disks or kneading elements, are welded onto the hollow shaft.

The length of the shaft for which the method can be used is restricted by the range of the sensor in particular. The more precisely the angle between end face and shaft casing is made, i.e. the closer said angle lies to 90°, the greater the range is as well. In the case of a deviation from the right angle, the signals transmitted by the sensor are transmitted in the direction of the shaft surface, and so said signals do not reach through the casing of the shaft over the entire length thereof. It is for this reason that greater precision of the angle between end face and casing lateral area is required as the shaft length increases. This precision in alignment can also be achieved by the insertion of an attachment wedge in the case of a deviation of the angle. To this end, it is necessary to detect the precise angle between end face and casing for each measurement position in order then to select the fitting attachment wedge. In doing so, the attachment wedge material should be selected such that it has sound properties that are as similar as possible to those of the hollow shaft.

In order to preclude measurement errors, it is furthermore advantageous if the sensor is placed onto the end face of the hollow shaft using a coupling agent. In doing so, the coupling agent is preferably selected such that it has similar sound properties to those of the material of the shaft. If use is made of an attachment wedge, the coupling agent is introduced between sensor and coupling wedge and between coupling wedge and shaft.

Furthermore, the method is particularly suitable for hollow shafts which are made of a metallic material. Here, e.g. iron-containing metals, e.g. steels, or else aluminum are suitable materials for the hollow shaft.

In order furthermore to preclude measurement errors, it is preferable for the end face of the shaft not to be clad. The end face of the hollow shaft onto which the sensor for the measurement is placed is preferably made of solid matter or welded. The signal is not reflected at a defect-free welding seam either, and so the welding seams are not interpreted as defects in the shaft.

Exemplary embodiments of the invention are illustrated in the figures and will be explained in more detail in the following description.

In detail:

FIG. 1 illustrates a cutaway of a hollow shaft with a sensor placed thereon.

Figure 1:
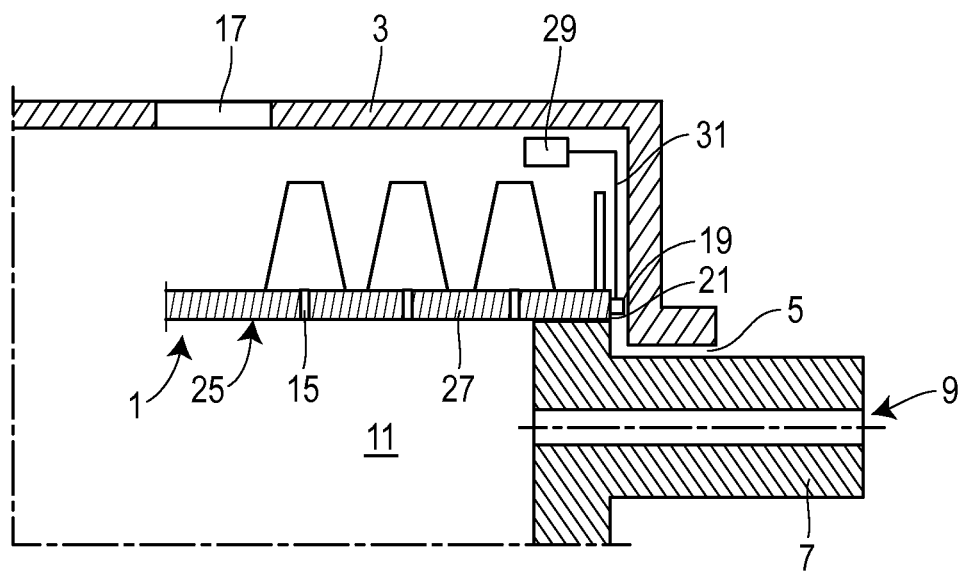
FIG. 1 shows a cutaway of a hollow shaft with a sensor placed thereon.

Hollow shafts 1 are used in a multiplicity of apparatuses. By way of example, such apparatuses include mixers, kneaders or dryers, in which material is conveyed or circulated. In order to ensure the functionality of the apparatus, the hollow shaft 1 is, in the process, usually enclosed by a housing 3. At least on the one side, the housing 3 has a passage 5, through which a shaft journal 7 is routed. By way of example, the shaft journal 7 is connected to a drive, e.g. a motor and a transmission. The hollow shaft 1 can be made to rotate by the shaft journal 7. At the end lying opposite to the drive, the hollow shaft 1 is for example equipped with a second shaft journal, which only serves for mounting purposes. In addition to a shaft journal 7, as illustrated in FIG. 1, the hollow shaft 1 can however be mounted and driven in any other fashion known to a person skilled in the art.

As a result of embodying the shaft as a hollow shaft 1, it is possible, for example, to allow a tempering medium to flow though said hollow shaft 1, in order to control the temperature of a material, which should be transported, circulated or conveyed with the aid of the hollow shaft 1, contained in the apparatus. By way of example, in this respect it is possible to form a channel 9 in the shaft journal 7. A tempering medium, e.g. steam, water or a thermal oil, can be routed through the channel 9 into the space 11 enclosed by the hollow shaft and it can flow through the hollow shaft.

In order to ensure the functionality of the hollow shaft 1 for conveying, mixing or kneading, functional elements 13 are preferably attached to the hollow shaft 1. By way of example, the functional elements 13 can be paddles, disks or kneading elements. The type of the functional elements 13 determines the purpose of the apparatus in this case. By way of example, if the apparatus is used as a kneader, the functional elements 13 are preferably kneading elements. If the apparatus is used as a dryer, disks or paddles are preferably provided as functional elements 13.

Particularly if the hollow shaft 1 is used in an apparatus for drying it is advantageous if the temperature of the functional elements 13 can likewise be controlled. To this end, it is possible, for example, to design the functional elements 13 to be hollow and to connect these to the inner space 11 in the hollow shaft 1 via channels 15. Tempering medium can flow out of the space 11 into the functional elements 13 with a hollow design through the channels 15. The functional elements 13 are preferably equipped with a second channel 15, through which the tempering medium can again return to the space 11 in the hollow shaft 1. By way of example, the channels 15 can be embodied in the form of a bore.

Particularly when using the apparatus comprising the hollow shaft 1 for methods that require high through-puts or in which large amounts should be processed, the apparatus has a correspondingly large design. Thus, for example, the hollow shaft 1 can have lengths in the range between 2 and 16 m. Correspondingly large apparatuses are for example used in the production of poly(meth)acrylates, which, as superabsorbers, for example find use in sanitary products. Here, the hollow shafts 1 are used both in kneading reactors, in which the poly(meth)acrylates are produced, and in dryers that are used for further processing. In order to obtain simple access to the shaft, without respectively having to open the apparatus and remove a housing cover, which may weigh up to several tons and is accordingly difficult to handle, a manhole 17 is for example formed in the housing 3, said manhole being dimensioned such that a person can climb into the apparatus through the manhole 17. By way of example, this is necessary for occasional inspections in order to determine whether damage has occurred on the hollow shaft 1 or on the functional elements 13 as a result of the operation.

However, fine cracks in particular, which can lead to a failure of the hollow shaft 1, cannot be immediately identified in a conventional manner. To this end, measurement methods have to be used, for example ultrasound measurement methods, in which an ultrasound signal is transmitted into the shaft and an echo of the signal, reflected at a defect, e.g. a shrink hole or a crack, is received. The position of the defect can be identified from the propagation time of the signal between transmitting the signal and receiving the echo. Such a defect emerges if the propagation time of the signal does not correspond to the propagation time that would be necessary for penetrating the length of the shaft. In the case of hollow shafts, such measurement methods are usually carried out over the external diameter. This leads to a multiplicity of measurement positions being required in order to carry out an inspection of the hollow shaft 1. Moreover, the hollow shaft 1 is only poorly accessible through the manhole 17. In order to carry out a comprehensive inspection of the shaft, it would be necessary to open the housing 3 in order thus to obtain access to the shaft.

Hence, according to the invention, a sensor 19 is positioned at an end face 21 of the hollow shaft 1 for detecting defects. In doing so, the sensor 19 is positioned between the outer face 23 and the inner face 25 of the casing 27 of the hollow shaft 1. In order to measure over the whole length of the hollow shaft 1, it is necessary for the angle between end face 21 and outer face 23 of the casing 27 to be precise so that the signal does not, as a result of a corresponding angle, reach the outer face of the casing and undergoes reflection there. The angle between end face 21 and outer face 23 of the casing therefore preferably lies in the range between 89 and 91°, more preferably in the range between 89.95 and 90.05°. This makes it possible to obtain reliable results by positioning the sensor 19 at the end face, even in the case of a casing 27 with a thin wall strength and a long shaft. In order to be able to read out the data captured by the sensor 19, the sensor 19 is usually connected to a control instrument 29. In general, the sensor 19 is connected to the control instrument 29 by a cable 31 in this case. However, alternatively, a wireless transmission is also possible. However, the use of a cable 31 is advantageous in that e.g. the necessary power supply for the sensor 19 can also be housed in the control instrument 29 and so the sensor 19 can be built in a more compact fashion. This makes it possible to use the sensor 19 even in the case of a narrow gap between shaft 1 and housing 3.

In order to obtain reliable measurement results, it is furthermore necessary for the hollow shaft 1 not to be clad at its end face 21. Reliable measurement results are only obtained if shaft 1 and end face 21 are made of solid matter. To this end, use can firstly be made of solid matter or, alternatively, use can also be made of a weld. All that is required is that no cavities, cracks or shrink holes, on which the signal of the sensor 19 can be reflected, are present in any form.

All that proves not to be possible using the method according to the invention is to conduct measurements in those regions in which the channels 15 are positioned. For this reason it is advantageous to position all channels 15 flush in one line. Since a crack, for example, will usually not extend in a straight line from one channel to the next channel 15, the channels 15 do not interfere with the measurement. Furthermore, it is advantageous to design the channels 15 to be as small as possible.

Alternatively, it is also possible, for example, to position the sensor 19 at a slight angle such that the signal is passed through between two channels 15. To this end it is possible, for example, to set different angles by using a suitable attachment, said angles positioning the sensor to respectively inspect the whole casing 27 of the hollow shaft 1. In this case, the sensor 19 is preferably attached to the end face 21 of the hollow shaft 1 via a suitable coupling agent, which has similar sound properties to the material of the hollow shaft 1. A corresponding attachment in the form of an attachment wedge can also be used if the angle between end face 21 and outer face 23 of the casing deviates from a right angle.

Figure 2:
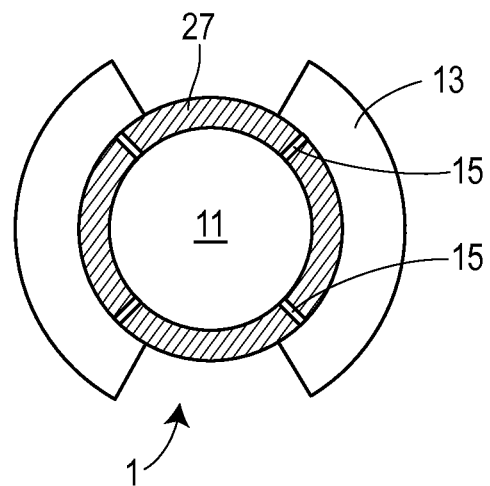
FIG. 2 shows a section through a hollow shaft.

FIG. 2 shows a section through a hollow shaft as illustrated in FIG. 1. The hollow shaft 1 has disks as functional elements 13, which are respectively connected to the space 11 in the interior of the hollow shaft 1 via two channels 15. For the purpose of measuring damage to the shaft, the sensor 19 is moved once around the circumference of the casing 27 and a measurement is carried out at each measurement position. To this end, it is possible to rotate the hollow shaft 1 a little further in each case and to keep the sensor 19 in one position. Alternatively, it is also possible to move the sensor 19 on a little further in each case when the shaft is stationary. It is only at the points at which the channels 15 are situated that no evaluable measurement result is obtained.

LIST OF REFERENCE SIGNS

1 Hollow shaft
3 Housing
5 Passage
7 Shaft journal
9 Channel
11 Space
13 Functional element
15 Channel
17 Manhole
19 Sensor
21 End face
23 Outer face
25 Inner face
27 Casing
29 Control instrument
31 Cable

The invention claimed is:

1. A method for detecting damage to a hollow shaft comprising:
    (a) positioning a sensor for transmitting and receiving a signal onto an end face of the hollow shaft,
    (b) transmitting a signal into solid material of the hollow shaft and receiving an echo of the signal,
    (c) determining a signal propagation time from the time of transmitting the signal until receiving the echo,
    (d) comparing the signal propagation time to a predetermined intended value and emitting a warning in the case of a deviation,
    wherein the sensor is positioned on the end face in a region between a radial distance of an inner face of a casing of the hollow shaft with respect to the axis and a radial distance of the outer face of the casing with respect to the axis on the end face of the shaft, the end face of the hollow shaft onto which the sensor is placed is made of solid matter or a welded material, and the end face of the shaft has an angle with respect to the axis of the shaft, which angle lies in the range between 89 and 91°.

2. The method according to claim 1, wherein the sensor is an ultrasound sensor.

3. The method according to claim 2, wherein the ultrasound sensor has an operating frequency in the range between 0.1 and 1 MHz.

4. The method according to claim 1, wherein the hollow shaft has a length in the range between 2 and 10 m.

5. The method according to claim 1, wherein the sensor is placed onto the end face of the hollow shaft using a coupling agent.

6. The method according to claim 1, wherein the hollow shaft is made of a metallic material.

7. The method according to claim 1, wherein the end face is integrally connected to a casing.

8. The method according to claim 1, wherein the hollow shaft is a shaft in a paddle dryer, a disk dryer, or a kneader.

9. The method according to claim 1, wherein functional elements are welded onto the hollow shaft.

10. The method according to claim 9, wherein the functional elements are paddles, disks, or kneading elements.

11. The method according to claim 6, wherein the metallic material is an iron-containing metal or aluminum.

* * * * *